United States Patent
Arai et al.

(10) Patent No.: US 7,381,467 B2
(45) Date of Patent: Jun. 3, 2008

(54) COMPOSITE PARTICLES COMPRISING FERROMAGNETIC PARTICLE, FLUORESCENT PIGMENT AND A SILICA COATING

(75) Inventors: Satoko Arai, Ibaraki (JP); Mikio Kishimoto, Ibaraki (JP); Kenji Kohno, Ibaraki (JP); Masahiro Kusumoto, Tsuruga (JP); Yoshiaki Nishiya, Tsuruga (JP)

(73) Assignee: Hitachi Maxell, Ltd., Osaka (JP)

( * ) Notice: Subject to any disclaimer, the term of this patent is extended or adjusted under 35 U.S.C. 154(b) by 215 days.

(21) Appl. No.: 11/081,537

(22) Filed: Mar. 17, 2005

(65) Prior Publication Data
US 2006/0062999 A1 Mar. 23, 2006

(30) Foreign Application Priority Data
Mar. 19, 2004 (JP) ............................ P2004-079391

(51) Int. Cl.
*B32B 5/16* (2006.01)
(52) U.S. Cl. ........................................ 428/403; 428/404
(58) Field of Classification Search ................ 428/403, 428/404, 405, 406, 900
See application file for complete search history.

(56) References Cited

U.S. PATENT DOCUMENTS 5,395,688 A * 3/1995 Wang et al. ................. 428/327
6,268,222 B1 7/2001 Chandler et al.
6,548,264 B1 * 4/2003 Tan et al. .................... 435/7.21
7,214,427 B2 * 5/2007 Huang et al. ............... 428/402
2003/0190628 A1 10/2003 Nakao et al.
2005/0009082 A1 1/2005 Nakao et al.
2006/0078734 A1 * 4/2006 Braune et al. .............. 428/403

FOREIGN PATENT DOCUMENTS

| JP | 6-273384 A | 9/1994 |
| JP | 2002-311027 A | 10/2002 |
| JP | 2003-270154 A | 9/2003 |
| JP | 3468750 B2 | 9/2003 |
| JP | 2004-305055 A | 11/2004 |

* cited by examiner

*Primary Examiner*—H. T Le
(74) *Attorney, Agent, or Firm*—Birch, Stewart, Kolasch & Birch, LLP

(57) ABSTRACT

The present invention provides composite particles which have magnetism and simultaneously emit fluorescence with a variety of wavelengths, and which are suitable for use in the fields of biology, biochemistry or the like. The composite particles of the present invention comprise ferromagnetic iron oxide particles, fluorescent pigment particles and silica, and have an average particle size of 1 to 10 μm, a coercive force of 2.39 to 11.94 kA/m (30 to 150 oersted), saturation magnetization of 0.5 to 40 A.m$^2$/kg (0.5 to 40 emu/g). The peak value of the wavelength of fluorescence from the composite particle is in the range of 350 to 750 nm, when the composite particle is excited by light with a wavelength of 250 to 600 nm.

5 Claims, 4 Drawing Sheets

PRIOR ART

US 7,381,467 B2

COMPOSITE PARTICLES COMPRISING FERROMAGNETIC PARTICLE, FLUORESCENT PIGMENT AND A SILICA COATING

BACKGROUND OF THE INVENTION

The present application is filed claiming the priority based on the Japanese patent application No. 2004-079391, which is herein incorporated by reference in its entirely.

FIELD OF THE INVENTION

The present invention relates to composite particles each of which has magnetism and simultaneously emits fluorescence with a different wavelength, and particularly to composite particles suitable for use in the fields of biology, biochemistry or the like.

In the fields of medical diagnoses and environmental assessment, subject substances in samples hitherto have been analyzed by taking advantage of specific reactions between labeled substances and substances immobilized on beads or plates. In such analyses, fluorescent materials are frequently used as labeling substances. In this case, a subject substance is analyzed by reacting a bead having a probe immobilized thereon, with the subject substance labeled with a fluorescent material; removing non-specific substances by washing; exciting the bead by irradiating with light; and detecting the wavelength and intensity of fluorescence from the bead to thereby analyze the subject substance.

In the analysis of a subject substance by this method, the use of beads labeled with fluorescent dyes is already known (cf. Patent Literature 1). In particular, two different fluorescent dyes in the variable ratio are fixed on beads to make it possible to discriminate the beads. Thus, the analysis is made by contrasting fluorescent signals from the beads with a fluorescent signal from a subject substance. In this method, a subtle difference in fluorescent intensity between the two different fluorescent dyes is detected, and therefore, highly sensitive detection is required, which leads to the need of an expensive apparatus.

On the other hand, silica beads containing fluorescent pigment molecules are known (cf. Patent Literature 2). The silica beads contain fluorescent pigment molecules which contain silicon atoms. Silica synthesized at a room temperature tends to be porous, and thus, the fluorescent pigment molecules can be captured in the pores of such silica. However, the fluorescent pigment molecules easily leave from the pores of the silica when the silica is dispersed in a solvent.

There are further known beads each of which has, on the surface thereof, semiconductor nano particles of cadmium selenide with a particle size of 1 to 10 nm (cf. Patent Literature 3). The beads of this type are characterized by utilizing the properties of the semiconductor nano particles: that is, the wavelengths of fluorescence from the semiconductor nano particles change depending on the particle sizes thereof. In particular, each of the beads comprises a polystyrene bead and semiconductor nano particles with a particle size far smaller than that of the polystyrene bead, bound to the surface of the polystyrene bead. When the beads of this type are used in a flow cytometry, there is a danger of the semiconductor nano particles' leaving from the polystyrene bead. In addition, the beads of this type must be subjected to centrifugal separation for recovery, since they are formed of polystyrene. Therefore, the beads of this type are hard to handle.

As mentioned above, the conventional beads containing fluorescent materials have suffered from the foregoing problems, i.e., the leaving of the fluorescent materials, the poor recovery of the beads, the need of expensive detection apparatuses, etc.

Patent Literature 1: the publication of Patent Registration No. 3468750 (page 3)

Patent Literature 2: the publication of JP-A-2003-270154 (pages 2 and 3)

Patent Literature 3: the publication of JP-A-2002-311027 (pages 2 to 4)

SUMMARY OF THE INVENTION

Under the foregoing circumstances, an object of the present invention is to provide composite particles which are suitable for use in the fields of biology, biochemistry or the like, and which can overcome the above problems, i.e., the leaving of fluorescent materials, the poor recovery of beads, the need of an expensive detection apparatus, etc.

BRIEF DESCTIPTION OF THE DRAWINGS

DETAILED DESCRIPTION OF THE PREFERRED EMBODIMENTS

Figure 1:
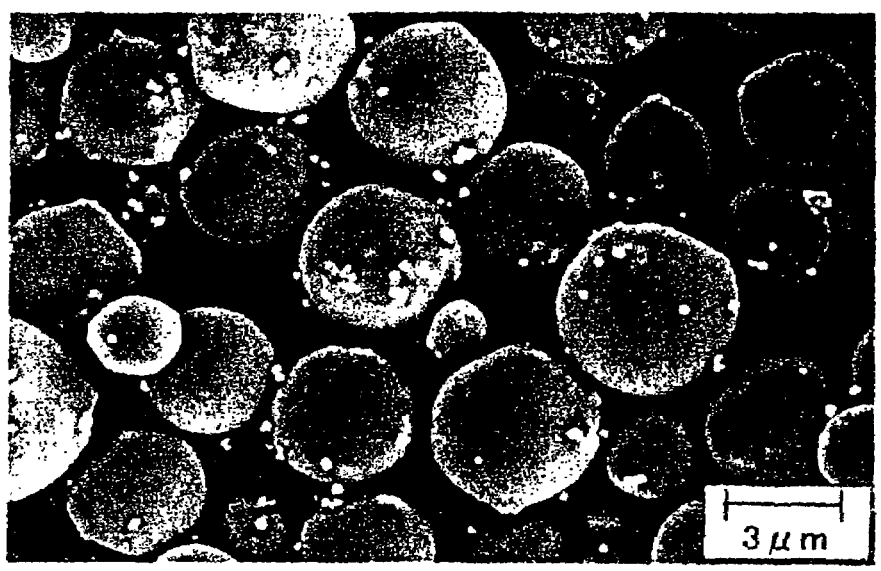
FIG. 1 shows the photograph of composite particles obtained in Example 1, taken with an electron microscope.

The present inventors have intensively researched in order to solve the foregoing problems and finally found out that composite particles particularly suitable for use in the fields of biology, biochemistry or the like can be obtained by integrating ferromagnetic iron oxide particles, fluorescent pigment particles and silica, in particular, by coating both the ferromagnetic iron oxide particles and the fluorescent pigment particles with the silica to thereby integrate both the particles, and also found that the composite particles, thus obtained, are advantageous in the following points: both of the particles are hardly separated from each other; the composite particles have magnetism and simultaneously emit fluorescence with a variety of wavelengths; and the composite particles are easily recovered because of their magnetism and can be discriminated because of their fluorescent properties, without the need of an expensive detection apparatus.

There is no particular limit in selection of the ferromagnetic iron oxide particles for use in the composite particles. For example, magnetite particles, gamma hematite particles, magnetite-alpha hematite intermediate iron oxide particles, gamma hematite-alpha hematite intermediate iron oxide particles, rare earth-iron-garnet particles, bismuth-substituted rare earth-iron-garnet particles and the like can be used as the ferromagnetic iron oxide particles. Among those, the rare earth-iron-garnet particles and the bismuth-substituted rare earth-iron-garnet particles are preferred, because their colors are yellow or yellowish green which can be used as basic colors for making it easy to impart color tones to composite particles integrated with fluorescent pigment particles.

Preferably, the average particle size of the ferromagnetic iron oxide particles is in the range of 0.02 to 1.0 μm. When the average particle size is too small, the ferromagnetic iron oxide particles tend to leave out from the pores of silica. On the other hand, when the average particle size is too large, it becomes hard to uniformly coat the ferromagnetic iron oxide particles and fluorescent pigment particles with silica.

As the fluorescent pigment particles, either organic pigment particles or inorganic pigment particles may be used. Particularly, organic fluorescent pigment particles are preferable, because they can provide vividly colored composite particles when integrated with yellow or yellowish green magnetic particles such as the rare earth-iron-garnet particles and the bismuth-substituted rare earth-iron-garnet particles.

The average particle size of the fluorescent pigment particles is preferably 0.05 to 5.0 μm. When the average particle size is too small, the intensity of fluorescence tends to be lower, and such particles tend to leave out from the pores of silica. When the average particle size is too large, it becomes hard to uniformly coat the ferromagnetic iron oxide particles and such fluorescent pigment particles with silica.

The wavelength of exciting light is preferably in the range of 250 to 600 nm. Within this range of excitation wavelengths, it is possible to use a variety of excitation light sources such as argon ion laser, xenon lamp, halogen lamp, etc. The wavelength of fluorescence is preferably in the range of 350 to 750 nm. Within this range of fluorescent wavelengths, the existing commercially available fluorescence detection apparatuses can be used. In addition, it becomes possible to confirm the fluorescence by visual observation, so that the composite particles can find a wider range of applications.

There is no particular limit in selection of the process for manufacturing the composite particles. For example, ferromagnetic iron oxide particles and fluorescent pigment particles are simply blended in the presence of silica as a binder to thereby integrate them; or, the mixed particles of ferromagnetic iron oxide particles and fluorescent pigment particles are coated with silica films to form globular composite particles. Particularly, the latter process is preferable, because the fluorescent pigment particles are enveloped in silica so that the deterioration of the pigment due to oxidation can be prevented, and because there can be surely solved the foregoing problem that the ferromagnetic iron oxide particles and the fluorescent pigment particles tend to leave out from the beads in use.

BEST MODES FOR CARRYING OUT THE INVENTION

The present invention provides composite particles which are obtained by integrating ferromagnetic iron oxide particles, fluorescent pigment particles and silica and which are characterized in that the peak value of the wavelength of fluorescence from the composite particles is in the range of 350 to 750 nm when the composite particles are excited by light with a wavelength of 250 to 600 nm. Most preferable are composite particles in which ferromagnetic iron oxide particles and fluorescent pigment particles are coated with silica films so as to be integrated together.

Preferably, the contents of the ferromagnetic iron oxide particles, the fluorescent pigment particles and the silica of the composite particles are 5 to 50 wt. % (preferably 10 to 40 wt. %), 5 to 50 wt. % (preferably 10 to 40 wt. %), and 20 to 90 wt. % (preferably 30 to 80 wt. %), respectively.

To fully exhibit the above mentioned effects, the average particle size of the composite particles is preferably 1 to 10 μm; the coercive force thereof is preferably 2.39 to 11.94 kA/m (30 to 150 oersted); and saturation magnetization thereof is preferably 0.5 to 40 $A.m^2/kg$ (0.5 to 40 emu/g).

Particularly, the average particle size of the composite particles is 2 to 8 μm; the coercive force thereof is 2.79 to 11.14 kA/m (35 to 140 oersted); and saturation magnetization thereof is 1 to 35 $A.m^2/kg$ (1 to 35 emu/g).

There is no particular limit in selection of the process for manufacturing the composite particles, and a suitable process may be employed according to the method of integrating ferromagnetic iron oxide particles, fluorescent pigment particles and silica.

Hereinafter, the process for manufacturing the composite particles of the present invention, in which rare earth-iron-garnet particles as the ferromagnetic iron oxide particles and fluorescent pigment particles are coated with silica films, is described. The rare earth-iron-garnet particles to be used in this process are prepared as follows.

<Process for Preparing Rare Earth-Iron-Garnet Particles>

The rare earth-iron-garnet particles can be industrially manufactured by the steps of (a) mixing an aqueous acidic solution containing rare earth elements and iron ions with an aqueous alkaline solution to obtain a coprecipitate of the rare earth elements and iron; (b) adding a fusing agent to the coprecipitate in the presence of water to form a suspension; (c) removing water from the suspension to obtain a mixture of the coprecipitate and the fusing agent; (d) heating the mixture at a temperature of 600 to 1,200° C. for crystallization of rare earth-iron-garnet particles; and (e) washing the particles with water to remove the fusing agent to obtain the rare earth-iron-garnet particles.

The above process for manufacturing the rare earth-iron-garnet particles is described in more detail, using yttrium (Y) as the rare earth element.

In the step (a), an aqueous acidic solution containing yttrium and iron, namely, an aqueous acidic solution containing the fundamental elements which compose yttrium-iron-garnet represented by the formula: $Y_3Fe_5O_{12}$, is mixed with an aqueous alkaline solution to form a coprecipitate of yttrium and iron, namely, the coprecipitate of the fundamental elements composing the yttrium-iron-garnet. The above aqueous acidic solution is an aqueous solution of an acidic salt of a metal which comprises yttrium and iron as essential components. While the kind of the acidic salt is not limited, a nitrate or a chloride which makes it hard for impurities to remain after washing with water is preferably used.

When a part of yttrium is substituted by bismuth (Bi), the heating temperature for producing yttrium-iron-garnet can be lowered, and the color tone of the resultant particles becomes brighter. The amount of yttrium to be substituted is preferably 1 to 50 mol. % determined by the equation of Bi/(Y+Bi) When the amount of Bi for substitution is too small, the effect of lowering the reaction temperature is poor.

When it is too large, undesirably, the saturation magnetization of the resultant composite particles excessively lowers.

As the aqueous alkaline solution, an aqueous alkaline solution of NaOH, KOH, ammonia or the like is used. Since both yttrium and an iron ion have valences of 3, at least three times of molar equivalent of alkaline ions are needed to form the coprecipitate.

However, preferably, the coprecipitate is formed in the presence of at least four times of molar equivalent of excessive alkaline ions in order to finally obtain yttrium-iron-garnet particles having larger saturation magnetization. While the upper limit of the amount of alkaline ions is not limited, the amount thereof is preferably at most twelve times of molar equivalent since too high concentration thereof lowers the efficiency of removing the impurities by washing with water.

In the step (b), the above coprecipitate is sufficiently washed with water to remove the excessive alkali ions, etc., and then, the fusing agent is added to the coprecipitate containing a such amount of water that allows the dissolution of the fusing agent, and the fusing agent is stirred and dissolved into the coprecipitate to form a homogeneous suspension of the fusing agent and the coprecipitate. When this dissolution by stirring is insufficient, it becomes difficult to obtain a homogeneous mixture of the coporecipitate and the fusing agent in the next step.

As the fusing agent, the chloride, bromide, iodide or fluoride of an alkali metal such as Na, K, Li or the like is preferably used. The amount of the fusing agent to be used is 100 wt. % or more, preferably 200 wt. % or more, based on the weight of finally obtained yttrium-iron-garnet particles. By doing so, the rare earth-iron-garnet particles most suitable for the purpose of the present invention can be obtained.

In the step (c), water is removed from the above suspension to obtain a homogeneous mixture of the coprecipitate and the fusing agent. To remove water, the suspension is directly heated in an air to a dryness so that only water is evaporated and removed.

In the step (d), the mixture is heated to form the crystallites of yttrium-iron-garnet in the fusing agent. The heating temperature is higher than the fusing point of the fusing agent, and may be appropriately selected within a range of 600 to 1,200° C., according to the type of the fusing agent.

Prior to the heat treatment, the mixture is previously molded by pressing or the like, so as to facilitate the reaction of the yttrium (Y) with the iron (Fe) in the fusing agent. This is effective to increase the saturation magnetization and develop the brighter color tone of the composite particles.

In the step (e), the yttrium-iron-garnet crystallites formed are washed with water to remove the fusing agent. The crystallites thus obtained are dried to obtain yellow or yellowish green fine particles which essentially comprise yttrium-iron-garnet represented by the formula: $R_3M_5O_{12}$, having an average particle size of 0.05 to 5 μm, a coercive force of 2.39 to 15.93 kA/m (30 to 200 oersted) and saturation magnetization of 1 to 30 A.m$^2$/kg (1 to 30 emu/g).

<Method of Forming Silica Films Over Rare Earth-Iron-Garnet Particles and Fluorescent Pigment Particles>

Next, silica films are formed over the rare earth-iron-garnet particles prepared as above and the fluorescent pigment particles so as to coat the same, as follows.

The formation of silica films is made on other ferromagnetic iron oxide particles and fluorescent pigment particles essentially in the same manner. Silica films are formed over the particles according to the following method.

The rare earth-iron-garnet particles prepared as above and the fluorescent pigment particles in a given ratio are mixed in a mortar. To the mixed particles is added a predetermined amount of an aqueous solution of sodium silicate so as to disperse the mixed particles in the aqueous solution of sodium silicate.

The weight ratio of the rare earth-iron-garnet particles to the fluorescent pigment particles is preferably 1/9 to 9/1, more preferably 2/8 to 8/2. When this ratio is outside the above range, the saturation magnetization of the composite particles is so small that the responsiveness of the composite particles to a magnetic field becomes lower, or that the emission of fluorescence is too weak to detect the fluorescence.

The amount of sodium silicate to be added is preferably 10 to 300 wt. %, more preferably 15 to 250 wt. %, in terms of $SiO_2$, based on the weight of the mixed particles. When this amount is small, the resultant composite particles tend to have larger saturation magnetization and emit intense fluorescence, but the mixed particles are hard to be uniformly coated with silica films. On the other hand, when this amount is large, the resultant composite particles have smaller saturation magnetization and lower responsiveness to a magnetic field, and the intensity of fluorescence becomes lower to make it difficult to detect the fluorescence.

Separately from the suspension of the mixed particles in the solution of sodium silicate, a given amount of a surfactant is dissolved in an organic solvent. Preferably, the organic solvent to be used has a low solubility in water, and preferable examples of such an organic solvent include benzene, toluene, xylene, n-hexane, isohexane, cyclohexane, ethyl acetate, butyl acetate and the like.

Preferable examples of the surfactant for use as an emulsifier include sorbitan fatty acid esters such as sorbitan monostearate, sobitan monolaurate, solbitan monopalmitate, sorbitan monooleate, sorbitan trioleate and the like.

The suspension of the mixed particles in the solution of sodium silicate is mixed with the solution of the surfactant in the organic solvent, and the mixture is stirred with a powerful stirrer such as a homomixer, homogenizer or the like, to prepare a W/O type emulsion. In this stage, the stirring time is preferably about 1 to 30 minutes, although depending on the power of the stirrer. When the stirring time is too short, it is hard to obtain emulsion particles with uniform particle sizes. When this time is too long, the rare earth-iron-garnet particles react with silica due to the stirring energy, and thus, the resultant particles can not have intended structures.

Each of the emulsion particles thus prepared has such a structure that the mixed particles and the aqueous solution of sodium silicate are enveloped in the surfactant in the organic solvent. Next, the suspension of the emulsion particles is added dropwise to an aqueous solution of ammonium salt.

The sodium silicate is dissolved in the water of the aqueous sodium silicate solution which is alkaline, but it is insoluble in a solution within the neutral region. When the aqueous sodium silicate solution is neutralized with the ammonium salt, silica is deposited. As a result, there are formed globular particles in which the mixed particles are coated with silica films as if enveloped in the silica films.

In this silica-depositing step, it is preferable to gradually deposit silica by adding dropwise the suspension of the emulsion particles to the aqueous solution of ammonium salt. The dropping time is preferably 10 minutes to 3 hours. When this time is short, the resultant silica films may have defectives or have uneven surfaces. On the other hand, when this time is long, no particular change is observed in the properties of the resultant silica films, but only the dropping time is meaninglessly prolonged.

As the ammonium salt, a sulfate or a carbonate is preferably used, and preferred examples thereof include ammonium carbonate, ammonium hydrogencarbonate, ammonium sulfate and the like.

The resultant particles are thoroughly washed with pure water, filtered and dried at 40° C. for 2 hours in vacuum, to obtain globular composite particles each of which has such a structure that the rare earth-iron-garnet particles and the fluorescent pigment particles are coated with silica, and which generally has an average particle size of 1 to 10 μm.

The composite particles thus manufactured in the present invention can be detected based on florescence from the fluorescent pigment particles, and therefore, it becomes possible to react a specific substance immobilized on the surface of the composite particle with a subject substance.

To immobilize, on the surface of the composite particle, the specific substance which is specifically bound to the subject substance, it is firstly needed to introduce a certain functional group into the surface of the composite particle. As the functional group, the use of an amino group, epoxy group, mercapto group, carboxyl group, hydroxyl group, vinyl group or (meth)acryl group is particularly effective.

<Method of Introducing Functional Group into Composite Particle>

There are various methods to introduce the above functional groups into the composite particles. Hereinafter, the method of introducing a functional group, using a silane coupling agent, is described as one of such examples.

Firstly, 1 to 40 wt. % of the composite particles as manufactured above are dispersed in water, based on the weight of the water, and a silane coupling agent solution is added to the aqueous dispersion. As the silane coupling agent solution, a commercially available one may be directly used, or may be diluted with water, alcohol, methyl ethyl ketone, toluene, benzene, dimethylformamide or dimethylsulfoxide, or a mixture thereof before use.

Some of the silane coupling agents have functional groups having affinity with biologically active substances, such as amino group, epoxy group, mercapto group, carboxyl group, hydroxyl group, vinyl group or (meth)acryl group. Specific examples of such silane coupling agents include N-2(aminoethyl)3-aminopropyltrimethoxysilane, N-2(aminoethyl)3-aminopropyltriethoxysilane, 3-glycidoxypropyltrimethoxysilane, 3-glycidoxypropylmethyldimethoxysilane, 3-mercaptopropyltrimethoxysilane, vinyltriethoxysilane and the like.

The amount of the silane coupling agent is preferably in the range of 0.01 to 20 wt. % based on the weight of the composite particles. When this amount is too small, the amount of a biological substance to be immobilized on the composite particle becomes smaller. When this amount is too large, the silane coupling agent is hard to uniformly bind to the surfaces of the composite particles, which, on the contrary, lowers the immobilizing efficiency.

The treating time is preferably about one to about 4 hours. When the treating time is too short, the binding of the silane coupling agent to the silica films on the surfaces of the composite particles is insufficient. When the treating time is too long, the above binding of the silane coupling agent is poor because of the adverse influence of alcohol which is produced during the reaction or because of the residual non-reacted alkoxy groups of the silane coupling agent.

The mixture treated as above are washed with water, filtered and dried to obtain composite particles, to the surfaces of which the functional groups of the silane coupling agent are bound.

The composite particles having the functional groups introduced thereinto make it possible to analyze a subject substance which is specifically bound to a substance immobilized on the surface of the composite particle, by a detection method utilizing fluorescence from the composite particle. In addition, the composite particles can be easily operated by using a magnetic field, since the composite particles have magnetism.

In concrete, optional substances can be easily immobilized on the composite particles. In particular, optional substances are immobilized on the composite particles having functional groups introduced thereinto, and such composite particles are collected to one site by utilizing a magnetic field, to thereby readily remove the non-reacted products. When the optional substances immobilized on the composite particles are reacted with the subject substances, their reaction can be easily carried out by utilizing a magnetic field as well.

Hereinafter, the process of manufacturing composite particles, which comprises the steps of preparing rare earth-iron-garnet particles or magnetite particles as the ferromagnetic iron oxide particles, and coating the ferromagnetic iron oxide particles and fluorescent pigment particles with silica, and the method of introducing functional groups into the surfaces of the composite particles, are described in more detail.

EXAMPLE 1

<Preparation of Rare Earth-Iron-Garnet Particles>

The preparation of rare earth-iron-garnet particles using yttrium as the rare earth element is described.

A solution of yttrium nitrate (0.1 mol) and iron nitrate (0.1785 mol) in water (2,000 cc) was mixed with a 12N nitric acid solution (100 cc) of bismuth nitrate (0.007 mol). The resulting aqueous nitrate solution was added dropwise to an aqueous solution of sodium hydroxide (3.415 mol) in water (2,000 cc) over about 30 minutes under stirring, to form a coprecipitate of yttrium, bismuth and iron. The coprecipitate was washed with water until the pH thereof reached the neutral region, and filtered to collect the coprecipitate. The coprecipitate was put in another vessel, and potassium bromide (0.857 mol) as a fusing agent and water (500 cc) were added. The mixture was stirred until potassium bromide was dissolved in water, to thereby obtain a suspension in which the coprecipitate was homogenously dispersed in the aqueous potassium bromide solution.

Next, the suspension was poured onto a vat and dried at 90° C. to remove water. Thus, a homogenous mixture of the coprecipitate and potassium bromide was obtained. The mixture was slightly crushed in a mortar and then subjected to press molding. The resultant molded matter was put in a crucible and subjected to a heat treatment at 850° C. for 2 hours, to thereby precipitate yttrium-iron-garnet particles in potassium bromide. Finally, the heat-treated particles were washed with water to dissolve and remove potassium bromide.

The resultant yttrium-iron-garnet particles in which a part of yttrium is substituted with bismuth (hereinafter referred to as bismuth-substituted yttrium-iron-garnet particles) had globular or ellipsoidal shapes with an average particle size of 0.32 μm, having a coercive force of 5.17 kA/m (65 oersted) and saturation magnetization of 24.3 A.m²/kg (24.3 emu/g), and taking a color tone of yellowish green.

<Manufacturing of Composite Particles Emitting Yellow Fluorescence>

The above bismuth-substituted yttrium-iron-garnet particles were used as the ferromagnetic iron oxide particles, and yellow fluorescent pigment particles with an average particle size of 1 μm which emitted yellow fluorescence ("SW-15N" manufactured by SINLOIHI Co., Ltd.) were used as the organic fluorescent pigment particles.

The bismuth-substituted yttrium-iron-garnet particles (10 g) and the yellow fluorescent pigment particles (10 g) were dispersed in pure water (130 g). Sodium silicate (21.9 g) was dissolved in this dispersion of the mixed particles. Separately, sorbitan monolaurate (7.0 g) as a surfactant was dissolved in hexane (470 cc). This surfactant solution was mixed with the dispersion of the mixed particles in which sodium silicate was dissolved. The resulting mixed solution was stirred and dispersed with a homomixer for 10 minutes to obtain an emulsion dispersion.

Next, ammonium sulfate (300 g) was dissolved in pure water (1,500 cc). The above emulsion dispersion was added dropwise to the ammonium sulfate solution being stirred, in about 30 minutes. After the completion of the addition, the mixture was further stirred for one hour. By this neutralization with ammonium sulfate, silica was deposited as if enclosing the bismuth-substituted yttrium-iron-garnet particles and the fluorescent pigment particles, to form silica films thereon.

The composite particles thus obtained were globular particles with an average particle size of about 5 μm, having a coercive force of 3.98 kA/m (50 oersted) and saturation magnetization of 9.5 A.m²/kg (9.5 emu/g). The composite particles were found to have structures in each of which the aggregate of the bismuth-substituted yttrium-iron-garnet particles and the fluorescent pigment particles was coated with silica, from the photograph taken with an optical microscope and the photograph taken with an electron microscope shown in FIG. 1.

The composite particles (0.5 g) were charged in a cylindrical glass tube with a diameter of 10 mm, and pure water (5 g) was charged therein. The mixture in the glass tube was dispersed for 30 minutes with an ultrasonic disperser. After that, the dispersion removed from the ultrasonic disperser was placed on a position on a magnet creating a magnetic field with an intensity of 3,000 gauss. Then, the time required for a whole of the composite particles to completely precipitate was measured. As a result, it was 10 seconds.

Figure 2:
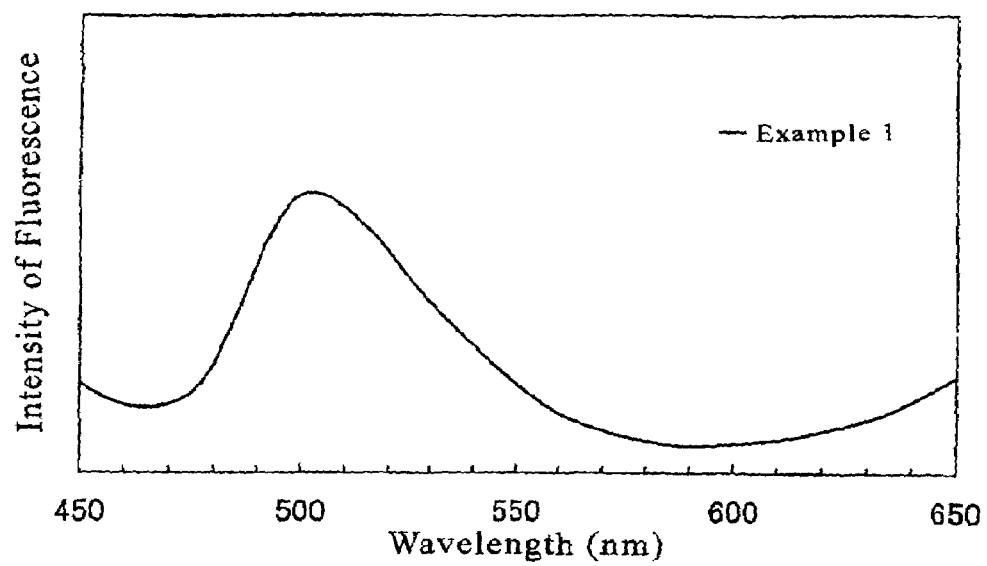
FIG. 2 shows the graph illustrating the fluorescent spectrum of the composite particles of Example 1.

Fluorescence from the composite particles was evaluated with a spectrofluometer Model No. EP-750 manufactured by Nippon Bunko (JASCO Corporation). The composite particles were put in a transparent nylon bag, which was secured on the solid sample holder of the spectrofluometer, and irradiated with light having an excitation wavelength of 356 nm, so as to measure the intensity of fluorescence with a wavelength of 450 to 650 nm from the composite particles. As a result, fluorescence having a peak at about 500 nm was observed, as shown in FIG. 2.

EXAMPLE 2

<Manufacturing of Composite Particles Emitting Orange Fluorescent>

The bismuth-substituted yttrium-iron-garnet particles prepared in Example 1 were used as the ferromagnetic iron oxide particles, and orange fluorescent pigment particles with an average particle size of 1 μm which emitted orange fluorescence ("SW-16N" manufactured by SINLOIHI Co., Ltd.) were used as the organic fluorescent pigment particles.

Composite particles were obtained in the same manner as in Example 1, except that the bismuth-substituted yttrium-iron-garnet particles (10 g) and the orange fluorescent pigment particles (15 g) were used.

The composite particles thus obtained were globular particles with an average particle size of about 4 μm, having a coercive force of 4.38 kA/m (55 oersted) and saturation magnetization of 9.2 A.m²/kg (9.2 emu/g). The composite particles were found to have structures in each of which the aggregate of the bismuth-substituted yttrium-iron-garnet particles and the fluorescent pigment particles was coated with silica, from the photograph taken with an optical microscope and the photograph taken with an electron microscope.

Figure 3:
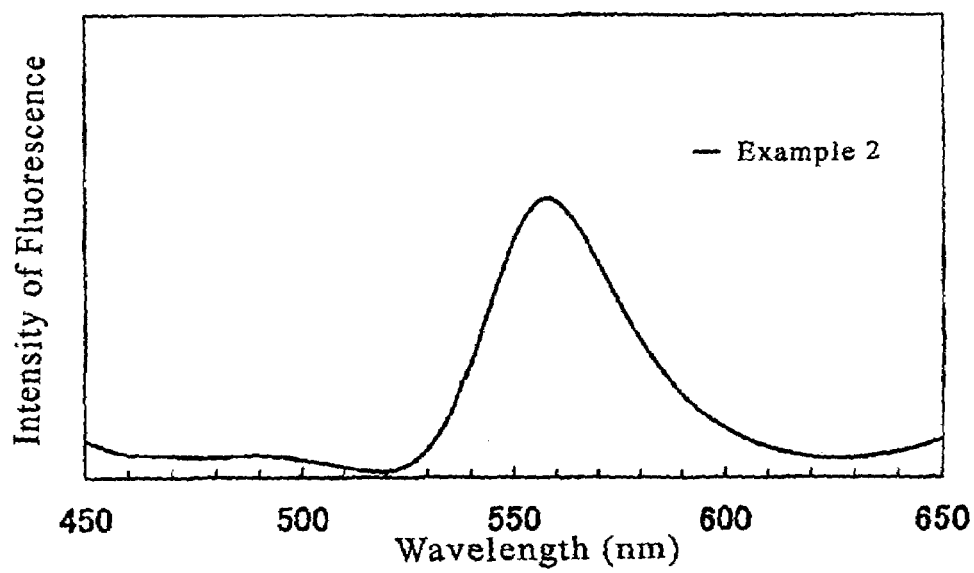
FIG. 3 shows the graph illustrating the fluorescent spectrum of the composite particles of Example 2.

The precipitating time of the composite particles measured in the same manner as in Example 1 was 11 seconds. As a result of the evaluation of fluorescence from the composite particles in the same manner as in Example 1, the fluorescence from the composite particles had a peak at about 560 nm, as shown in FIG. 3.

EXAMPLE 3

<Manufacturing of Composite Particles Emitting Red Fluorescent>

The bismuth-substituted yttrium-iron-garnet particles prepared in Example 1 were used as the ferromagnetic iron oxide particles, and red fluorescent pigment particles with an average particle size of 1 μm which emitted red fluorescence ("SW-13" manufactured by SINLOIHI Co., Ltd.) were used as the organic fluorescent pigment particles.

Composite particles were obtained in the same manner as in Example 1, except that the bismuth-substituted yttrium-iron-garnet particles (10 g) and the red fluorescent pigment particles (10 g) were used.

The composite particles thus obtained were globular particles with an average particle size of about 5 μm, having a coercive force of 4.38 kA/m (55 oersted) and saturation magnetization of 10.0 A.m²/kg (10.0 emu/g). The composite particles were found to have structures in each of which the aggregate of the bismuth-substituted yttrium-iron-garnet particles and the fluorescent pigment particles was coated with silica, from the photograph taken with an optical microscope and the photograph taken with an electron microscope.

Figure 4:
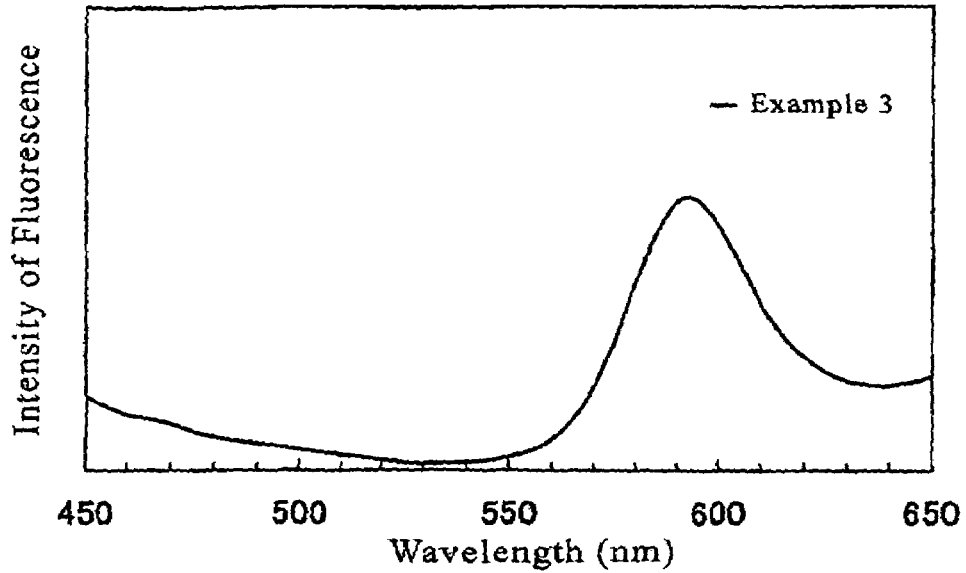
FIG. 4 shows the graph illustrating the fluorescent spectrum of the composite particles of Example 3.

The precipitating time of the composite particles measured in the same manner as in Example 1 was 10 seconds. As a result of the evaluation of fluorescence from the composite particles in the same manner as in Example 1, the fluorescence from the composite particles had a peak at about 600 nm, as shown in FIG. 4.

EXAMPLE 4

<Manufacturing of Composite Particles Emitting Purple Fluorescent>

The bismuth-substituted yttrium-iron-garnet particles prepared in Example 1 were used as the ferromagnetic iron oxide particles, and purple fluorescent pigment particles with an average particle size of 1 μm which emitted purple fluorescence ("SW-28" manufactured by SINLOIHI Co., Ltd.) were used as the organic fluorescent pigment particles.

Composite particles were obtained in the same manner as in Example 1, except that the bismuth-substituted yttrium-iron-garnet particles (10 g) and the purple fluorescent pigment particles (15 g) were used.

The composite particles thus obtained were globular particles with an average particle size of about 6 μm, having a coercive force of 4.77 kA/m (60 oersted) and saturation magnetization of 8.9 A.m$^2$/kg (8.9 emu/g). The composite particles were found to have structures in each of which the aggregate of the bismuth-substituted yttrium-iron-garnet particles and the fluorescent pigment particles was coated with silica, from the photograph taken with an optical microscope and the photograph taken with an electron microscope.

Figure 5:
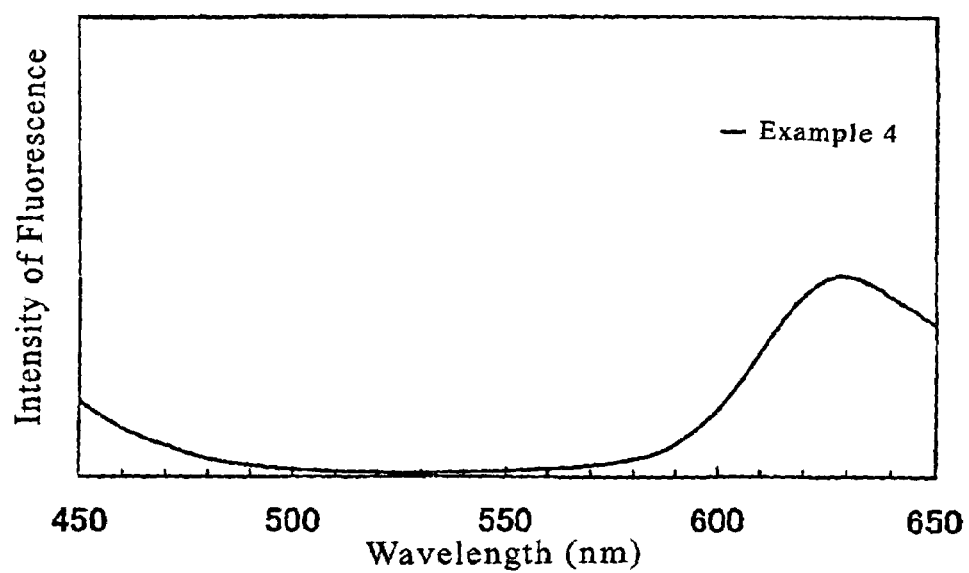
FIG. 5 shows the graph illustrating the fluorescent spectrum of the composite particles of Example 4.

The precipitating time of the composite particles measured in the same manner as in Example 1 was 11 seconds. As a result of the evaluation of fluorescence from the composite particles in the same manner as in Example 1, the fluorescence from the composite particles had a peak at about 630 nm, as shown in FIG. 5.

EXAMPLE 5

<Preparation of Magnetite Particles>

Ferrous sulfate (FeSO$_4$·7H$_2$O) (100 g) was dissolved in pure water (1,000 cc). Sodium hydroxide (28.8 g) was dissolved in pure water (500 cc) so as to be equivalent in mole to the ferrous sulfate. Next, the aqueous sodium hydroxide solution was added dropwise to the aqueous ferrous sulfate solution being stirred in one hour, to form a precipitate of ferrous hydroxide. After the completion of the addition, the suspension containing the precipitate of ferrous hydroxide was heated to 85° C. under stirring. The suspension was oxidized for 8 hours while an air was being blown into the suspension heated to 85° C., at a rate of 200 L/hr. with an air pump. Thus, magnetite particles were produced.

The magnetite particles had substantially globular shapes with an average particle size of about 0.28 μm. The particle size of the magnetite particles was determined by measuring the particle sizes of about 300 magnetite particles on the photograph taken with a transmission electron microscope, and averaging the resulting particle sizes.

<Manufacturing of Composite Particles Emitting Yellow Fluorescence>

The above magnetite particles were used as the ferromagnetic iron oxide particles, and yellow fluorescent pigment particles with an average particle size of 1 μm which emitted yellow fluorescence ("SW-15N" manufactured by SIN-LOIHI Co., Ltd.) were used as the organic fluorescent pigment particles.

The magnetite particles (10 g) and the yellow fluorescent pigment particles (10 g) were dispersed in pure water (130 g). Sodium silicate (21.9 g) was dissolved in this dispersion of the mixed particles. Separately, sorbitan monolaurate (7.0 g) as a surfactant was dissolved in hexane (470 cc). This surfactant solution was mixed with the dispersion of the mixed particles in which sodium silicate was dissolved. The resulting solution mixture was stirred and dispersed with a homomixer for 10 minutes to obtain an emulsion dispersion.

Next, ammonium sulfate (300 g) was dissolved in pure water (1,500 cc). The above emulsion dispersion was added dropwise to the ammonium sulfate solution being stirred in about 30 minutes. After the completion of the addition, the mixture was further stirred for one hour. By this neutralization with ammonium sulfate, silica was deposited as if enclosing the magnetite particles and the fluorescent pigment particles, to form silica films thereon.

Figure 6:
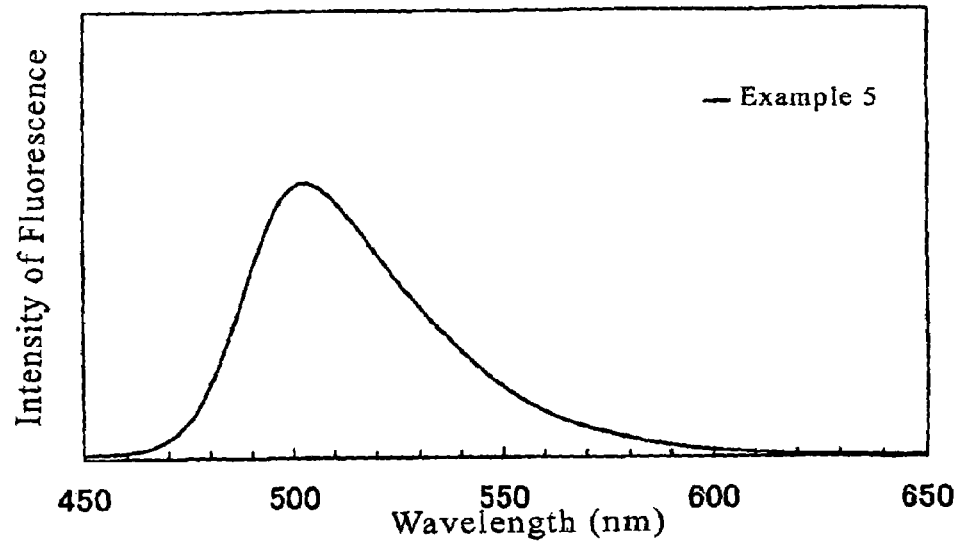
FIG. 6 shows the graph illustrating the fluorescent spectrum of the composite particles of Example 5.

The composite particles thus obtained were globular particles with an average particle size of about 5 μm, having a coercive force of 7.95 kA/m (100 oersted) and saturation magnetization of 12.0 A.m$^2$/kg (12.0 emu/g). The composite particles were found to have structures in each of which the aggregate of the magnetite particles and the fluorescent pigment particles was coated with silica, from the photograph taken with an optical microscope and the photograph taken with an electron microscope. The precipitating time of the composite particles measured in the same manner as in Example 1 was 9 seconds. As a result of the evaluation of fluorescence from the composite particles in the same manner as in Example 1, the fluorescence from the composite particles had a peak at about 500 nm, as shown in FIG. 6.

EXAMPLE 6

<Treatment for Introducing a Functional Group into a Composite Particle>

As a method of introducing a functional group into the composite particle, a treatment with a silane coupling agent having an amino group as a functional group is described.

The composite particles emitting yellow fluorescence (10 g) obtained in Example 1 were dispersed in pure water (25 g). N-2(Aminoethyl)3-aminopropyl-trimethoxysilane (0.2 g) having an amino group at the end was added to the dispersion which was being stirred. After the addition, the mixture was stirred for 3 hours, washed with water, filtered and dried at 110° C. for 4 hours to obtain composite particles having amino groups introduced thereinto.

The composite particles which had the amino groups introduced thereinto as above are suitable as carriers for use in immobilizing biologically active substances such as proteins, glycoproteins and saccharides, which had actions as enzymes, antibodies and coenzymes, and are most suitable as carriers for immobilizing enzymes.

In this Example, the amino group of the silane coupling agent is introduced as a functional group into the composite particle. Other than this, silane coupling agents having functional groups such as an epoxy group, mercapto group, carboxyl group, hydroxyl group, vinyl group, (meth)acryl group and the like, which have affinity to biologically active substances, can be used. The use of these silane coupling agents make it possible to introduce a variety of functional groups as above into the composite particles.

In the present invention, a chemical bond is formed between the silanol group of the silane coupling agent and the silica on the surface of the composite particle, and the functional group as mentioned above is efficiently introduced into the composite particle so as to direct outward from the magnetic particle.

The responsiveness of the above composite particles having the amino groups introduced thereinto, to a magnetic field, and fluorescence therefrom were evaluated in the same manners as in Example 1. As a result, the composite particles showed similar responsiveness to the magnetic field and similar fluorescence to those of the composite particles of Example 1. That is, the composite particles having functional groups introduced thereinto can find more applications, since such composite particles can be used to immobilize enzymes, etc., while maintaining the magnetic field responsiveness and the fluorescent properties which the composite particles of the present invention possess.

COMPARATIVE EXAMPLE 1

Composite particles of fluorescent pigment particles and silica were obtained in the same manner as in Example 1, except that no bismuth-substituted yttrium-iron-garnet particle as the ferromagnetic iron oxide particle was used, and that only yellow fluorescent pigment particles (20 g) were used.

The composite particles thus obtained were globular particles with an average particle size of about 6 μm, having no magnetism. The composite particles were found to have structures in each of which the aggregate of the fluorescent pigment particles was coated with silica, from the photograph taken with an optical microscope and the photograph taken with an electron microscope.

Figure 7:
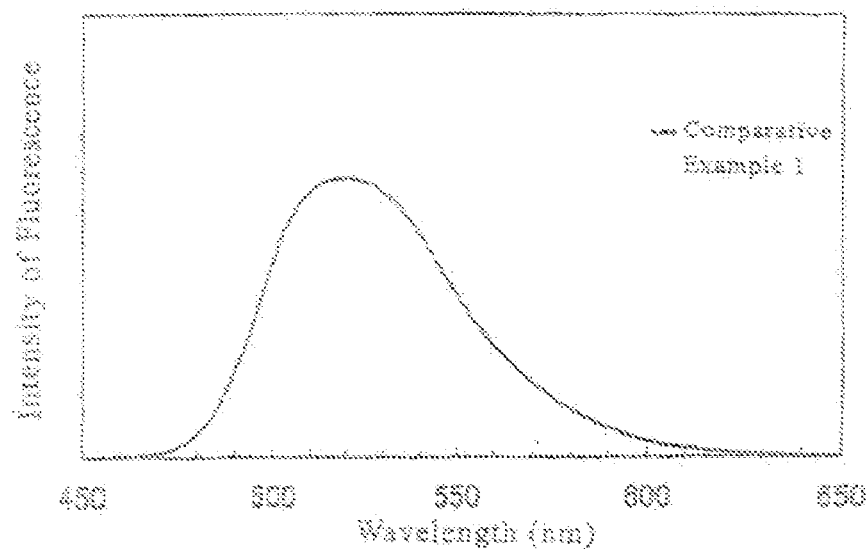
FIG. 7 shows the graph illustrating the fluorescent spectrum of the composite particles of Comparative Example 1.

The precipitating time of the composite particles measured in the same manner as in Example 1 was 250 seconds. As a result of the evaluation of fluorescence from the composite particles in the same manner as in Example 1, the fluorescence from the composite particles had a peak at about 520 nm, as shown in FIG. 7.

COMPARATIVE EXAMPLE 2

Composite particles of ferromagnetic iron oxide particles and silica were obtained in the same manner as in Example 1, except that no yellow fluorescent pigment particle was used, and that only the bismuth-substituted yttrium-iron-garnet particles (20 g) were used as the ferromagnetic iron oxide particles.

The composite particles thus obtained were globular particles with an average particle size of about 5 μm, having a coercive force of 3.98 kA/m (50 oersted) and saturation magnetization of 9.8 A.m$^2$/kg (9.8 emu/g). The composite particles were found to have structures in each of which the aggregate of the bismuth-substituted yttrium-iron-garnet particles was coated with silica, from the photograph taken with an optical microscope and the photograph taken with an electron microscope.

Figure 8:
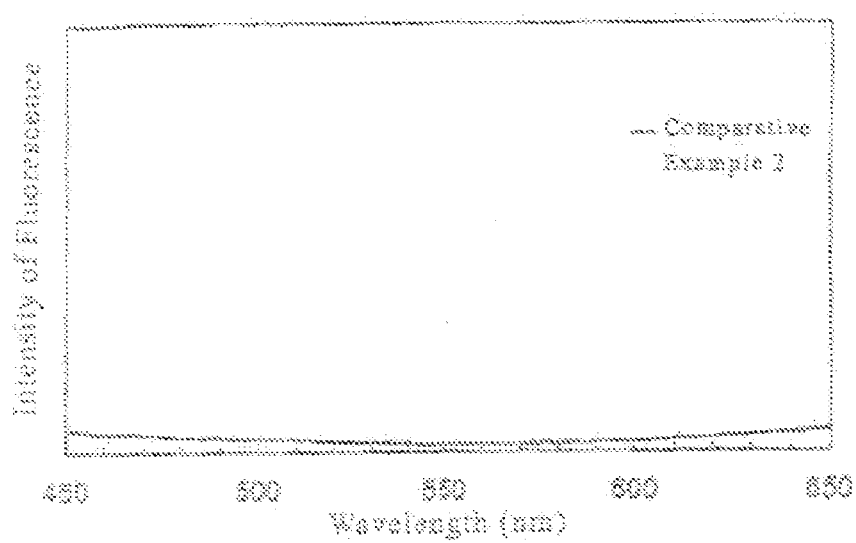
FIG. 8 shows the graph illustrating the fluorescent spectrum of the composite particles of Comparative Example 2.

The precipitating time of the composite particles measured in the same manner as in Example 1 was 10 seconds. As a result of the evaluation of fluorescence from the composite particles in the same manner as in Example 1, no fluorescence from the composite particles was observed within a wavelength range of 450 to 650 nm, as shown in FIG. 8.

The average particle sizes, coercive forces, saturation magnetization, precipitating time and the wavelengths ($\lambda_{Em}$) of the peaks of the fluorescent spectra of the composite particles of Examples 1 to 5 and Comparative Examples 1 and 2 are summarized in Table 1 below.

The average particle sizes, coercive force and saturation magnetization of the composite particles were determined as follows.

<Average Particle Size>

The photograph of the composite particles was taken with a scanning electron microscope, and the particle sizes of 50 composite particles on the photograph were measured, and averaged to get the average value.

<Coercive Force and Saturation Magnetization>

The coercive force and saturation magnetization of the composite particles were measured with a Vibrating Sample Magnetometer (manufactured by Toei Industry Co., Ltd.). The saturation magnetization was determined from the magnetized amount of the composite particles which were exposed to a magnetic field of 797 KA/m (10 kirooersted).

TABLE 1

| | Average particle size (μm) | Coercive force (KA/m) | Saturation magnetization (Am$^2$/Kg) | Precipitating time (sec.) | $\lambda_{Em}$ (nm) |
|---|---|---|---|---|---|
| Ex. 1 | 5 | 3.98 | 9.5 | 10 | 500 |
| Ex. 2 | 5 | 4.38 | 9.2 | 11 | 560 |
| Ex. 3 | 5 | 4.38 | 10.0 | 10 | 600 |
| Ex. 4 | 6 | 4.77 | 8.9 | 11 | 630 |
| Ex. 5 | 5 | 7.95 | 12.0 | 9 | 500 |
| C. Ex. 1 | 6 | — | — | 250 | 520 |
| C. Ex. 2 | 5 | 3.98 | 9.8 | 10 | — |

As is apparent from the above results, the composite particles of Examples 1 to 4 in each of which the rare earth-iron-garnet particles and the fluorescent pigment particles are coated with silica, and the composite particles of Example 5 in each of which the magnetite particles and the fluorescent pigment particles are coated with silica can be precipitated in shorter time by utilizing magnetic fields, and thus are proved to have higher responsiveness to magnetic fields, as compared with the composite particles of Comparative Example 1.

It is also clearly proved that the composite particles of Examples 1 to 4 and the composite particles of Example 5 show excellent fluorescent properties in addition to the higher responsiveness to magnetic fields. In contrast, the composite particles of Comparative Example 2 show responsiveness to a magnetic field, however, do not show any fluorescent property, and thus, can not be detected based on fluorescence.

As is understood from the foregoing descriptions, according to the present invention, the aggregate of fluorescent pigment particles and at least one type of ferromagnetic iron oxide particles selected from magnetite particles, gamma hematite particles, magnetite-alpha hematite intermediate iron oxide particles, gamma hematite-alpha hematite intermediate iron oxide particles, rare earth-iron-garnet particles, bismuth-substituted rare earth-iron-garnet particles and the like, is coated with silica. Thus, the present invention can provide composite particles which can be detected based on fluorescence emitting from themselves, while maintaining magnetism.

In the fields of biology, biochemistry or the like, by immobilizing a specific substance on the surface of the composite particle having the above structure, it becomes possible to analyze a subject substance which is specifically bound to the specific substance on the surface of the composite particle, detected from the wavelength of fluorescence from the composite particle. Further, the composite particles of the present invention have magnetism, and therefore make it easy to immobilize specific substances and to carry out reactions between the specific substances and subject substances by utilizing magnetic fields.

EFFECT OF THE INVENTION

As described above, the present invention can provide composite particles particularly suitable for use in the fields of biology, biochemistry or the like, and such composite particles are manufactured by integrating ferromagnetic iron oxide particles, fluorescent pigment particles and silica, especially by coating both the particles with silica, thereby integrating both the particles. Both the particles thus integrated do not easily leave from the resultant composite particles, and the composite particles thus obtained have magnetism and simultaneously emit fluorescence with a different wavelength, and are easily recovered because of their magnetism and are also easily detected because of the emission of fluorescent light, which advantageously leads to no need of an expensive apparatus for the detection thereof.

The invention claimed is:

1. A composite particle comprising a ferromagnetic iron oxide particle, a fluorescent pigment particle and silica, and having
an average particle size of 1 to 10 μm,
a coercive force of 2.39 to 11.94 kA/m (30 to 150 oersted),
saturation magnetization of 0.5 to 40 A.m$^2$/kg (0.5 to 40 emu/g) and
a structure in which the ferromagnetic iron oxide particle and the fluorescent pigment particle are coated with silica,
characterized in that the peak value of the wavelength of fluorescence from the composite particle is in the range of 350 to 750 nm when the composite particle is excited by light with a wavelength of 250 to 600 nm.

2. A composite particle according to claim 1, wherein the ferromagnetic iron oxide particle is at least one selected from the group consisting of a magnetic particle, gamma hematite particle, magnetite-alpha hematite intermediate iron oxide particle, gamma hematite-alpha hematite intermediate iron oxide particle, rare earth-iron-garnet particle and bismuth-substituted rare earth-iron-garnet particle, each of which has an average particle size of 0.2 to 1.0 μm.

3. A composite particle according to claim 1, wherein the fluorescent pigment particle is an organic fluorescent pigment having an average particle size of 0.5 to 5.0 μm.

4. A composite particle according to claim 1, wherein the contents of the ferromagnetic iron oxide particle, the fluorescent pigment particle and the silica are 5 to 50 wt. %, 5 to 50 wt. % and 20 to 90 wt. %, respectively.

5. A composite particle according to claim 1, wherein at least one functional group selected from the group consisting of an amino group, epoxy group, mercapto group, carboxyl group, hydroxyl group, vinyl group and (meth) acryl group is present on the surface of the composite particle.

* * * * *